United States Patent
Jacobs

(10) Patent No.: US 12,089,975 B2
(45) Date of Patent: Sep. 17, 2024

(54) X-RAY ANTI SCATTER GRID

(71) Applicant: KONINKLIJKE PHILIPS N.V., Eindhoven (NL)

(72) Inventor: Johannes Wilhelmus Maria Jacobs, Boxtel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 170 days.

(21) Appl. No.: 17/760,923

(22) PCT Filed: Sep. 10, 2020

(86) PCT No.: PCT/EP2020/075256
§ 371 (c)(1),
(2) Date: Mar. 16, 2022

(87) PCT Pub. No.: WO2021/052842
PCT Pub. Date: Mar. 25, 2021

(65) Prior Publication Data
US 2022/0338824 A1      Oct. 27, 2022

(30) Foreign Application Priority Data
Sep. 18, 2019   (EP) .................................... 19198035

(51) Int. Cl.
*A61B 6/00*     (2024.01)
*A61B 6/42*     (2024.01)
*G21K 1/02*     (2006.01)

(52) U.S. Cl.
CPC ............ *A61B 6/4291* (2013.01); *G21K 1/025* (2013.01)

(58) Field of Classification Search
None
See application file for complete search history.

(56) References Cited

U.S. PATENT DOCUMENTS

| 6,047,044 A | 4/2000 | Lehmann |
| 2018/0259463 A1 | 9/2018 | Yokoyama |
| 2020/0234839 A1* | 7/2020 | Choquette .............. G21K 1/025 |

FOREIGN PATENT DOCUMENTS

| CN | 105989905 A | 10/2016 |
| EP | 0967619 A2 | 12/1999 |

(Continued)

OTHER PUBLICATIONS

PCT International Search Report, International application No. PCT/EP2020/075256, Nov. 12, 2021.

(Continued)

*Primary Examiner* — Hoon K Song
(74) *Attorney, Agent, or Firm* — Larry Liberchuk

(57) ABSTRACT

The present invention relates to an X-ray anti-scatter grid (10). The anti-scatter grid comprises a plurality of primary septa walls (20), and a plurality of secondary septa walls (30). The plurality of primary septa walls comprise an X-ray absorbing material. The plurality of primary septa walls are substantially parallel to one another. The plurality of secondary septa walls are located between adjacent pairs of walls of the plurality of primary septa walls such that each secondary septa wall is located between an adjacent pair of walls of the plurality of primary septa walls. Each secondary septa wall of the plurality of secondary septa walls is formed from a plurality of columnar structures (40) extending between the plurality of primary septa walls. The plurality of columnar structures comprise an X-ray absorbing material.

11 Claims, 5 Drawing Sheets

(56) References Cited

FOREIGN PATENT DOCUMENTS

| WO | WO2018108853 A1 | 6/2018 |
| WO | WO2018194937 A1 | 10/2018 |

OTHER PUBLICATIONS

Alexeev T. et al., "A Novel Total Variation Based Ring Artifact Suppression Method for CBCT Imaging with Two-Dimensional Antiscatter Grids", Medical Physics 46 (5), 2189 (2019).

* cited by examiner

X-RAY ANTI SCATTER GRID

FIELD OF THE INVENTION

The present invention relates to an X-ray anti-scatter grid, a method of manufacturing an X-ray anti-scatter grid, and a method of manufacturing a plurality of secondary septa walls for an X-ray anti-scatter grid.

BACKGROUND OF THE INVENTION

When scattered X-rays from the patient are collected by the imaging detector, they do not provide any additional information about the anatomy of the patients, but they degrade the image quality by reducing the contrast and contrast-to-noise ratio (CNR) of the image. Hence anti-scatter grids (ASG) have been in use for a number of decades in medical X-ray imaging (e.g. digital radiography, fluoroscopic imaging, 3D X-ray) and X-ray Computer Tomography (CT) imaging to absorb scattered X-rays, and thereby improve image quality.

The use of 1D X-ray anti-scatter grids is well-established in X-ray imaging, but they suffer from too low an anti-scatter performance (too high a scatter-to-primary signal ratio (SPR), and too low a CNR) for next generation (spectral) 3D X-ray Cone-Beam CT (CBCT) and CT imaging systems.

An important requirement for spectral X-ray imaging is the provision of good discrimination between primary and scattered X-ray photons. A scattered X-ray photon has a lower (undefined) energy than the original primary X-ray photon, and therefore reduces the spectral energy resolution capability of the X-ray detector if such photons are not absorbed by the anti-scatter grid. Therefore, 2D DMLS tungsten grids have been introduced for CT imaging. But they suffer from a problem that the thick (≈100 µm) septa walls block the route towards smaller pixel (<1 mm) CT detectors. Thus, current 2D Direct Metal Laser Sintered (DMLS) tungsten CT ASGs are not compatible with smaller (<1 mm) pixel CT detectors because of the too thick (≈100 µm) septa walls. Another important disadvantage is the high manufacturing cost.

For 3D X-ray imaging (CBCT) an alternative 2D DMLS tungsten ASG grid has been proposed in WO2018194937A1. But such a structure causes grid line artifacts (GLA's) in X-ray images caused by the thick (≈100 µm) septa walls: see for example T. Alexeev et al., "A novel total variation based ring artifact suppression method for CBCT imaging with two-dimensional antiscatter grids", Medical Physics 46 (5), 2189 (2019). Other disadvantages again include high manufacturing costs and heavy weight.

EP0967619B1 describes an ASG fabrication method in which a high-energy laser beam is projected through a phase mask onto an X-ray transparent substrate in order to ablate portions of the substrate material followed by filling them with X-ray absorbing material. This process is critically dependent on maintaining a uniform laser fluence (energy density distribution) to all substrate parts and can lead to contamination of substrate and optical components. Furthermore, the laser-induced local increase of substrate temperature is very sensitive to the grid pattern and grid dimensions.

To aid in visualization of the structure of such anti-scatter grids, the following figures are presented. FIG. 2 shows a current state of the art 1D anti-scatter grid design for an X-ray system. Primary X-rays are shown at "A", with scatter X-rays shown at "B". The septa walls 20 are for example made from lead or other high-Z material, and have a spacing between adjacent walls of "D". FIG. 3 shows an equivalent 1D ASG, where there is an interspace material "A" between the septa walls 20. The height of the septa walls in the direction of the incident X-rays is "h" and the thickness of each wall is "d". FIG. 4 shows current state of the art ASGs in X-ray CT systems. FIG. 4A shows a 1D ASG, FIG. 4B shows a folded molybdenum-based 2D ASG and FIG. 4C shows a tungsten-based 2D ASG. The large 2D ASG shown at FIG. 4D, with expanded detail below, shows a 3D-printed 2D ASG see Dunlee DMLS tungsten CT grids, https://www.dunlee.com/a-w/3d-metal-printing/our-offer/anti-scatter-grids-for-ct.html.

However, as discussed above these 2D structures are very difficult and expensive to fabricate/manufacture.

There is a need to address these issues.

SUMMARY OF THE INVENTION

It would be advantageous to improved 2D X-ray anti-scatter grids.

The object of the present invention is solved with the subject matter of the independent claims, wherein further embodiments are incorporated in the dependent claims. It should be noted that the following described aspects and examples of the invention apply also to the X-ray anti-scatter grid, the method of manufacturing an X-ray anti-scatter grid, and the method of manufacturing a plurality of secondary septa walls for an X-ray anti-scatter grid.

In a first aspect, there is provided an X-ray anti-scatter grid, comprising:
  a plurality of primary septa walls; and
  a plurality of secondary septa walls.
The plurality of primary septa walls comprise an X-ray absorbing material. The plurality of primary septa walls are substantially parallel to one another. The plurality of secondary septa walls are located between adjacent pairs of walls of the plurality of primary septa walls such that each secondary septa wall is located between an adjacent pair of walls of the plurality of primary septa walls. Each secondary septa wall of the plurality of secondary septa walls is formed from a plurality of columnar structures extending between the plurality of primary septa walls. The plurality of columnar structures comprise an X-ray absorbing material.

In other words, a new design for a 2D anti-scatter grid is provided, that can be scaled to large areas, that takes a 1D grid made for example in a normal manner using established 1D manufacturing technology with for example lead septa, and adds to this to provide a 2D structure. The 2D structure is provided through locating x-ray absorbing columnar structures, that for example contain a high Z material, where each extends laterally from one primary septa wall to the next in a direction generally perpendicular to the direction of X-ray propagation, and where these columnar structures form secondary septa walls. Thus each secondary septa wall is located between adjacent walls of primary septa walls, with this applying across the x-ray anti-scatter grid. Each secondary septa wall is formed from columnar structures that extend from one primary septa wall to the adjacent primary septa wall, extending laterally in a direction generally perpendicular to the direction of X-ray propagation and thus a centre axis down each columnar structure is generally perpendicular to the primary septa walls.

To put this another way, starting from a conventional 1D grid based on primary septa walls formed for example by lead lamella, secondary grid septa walls are introduced in the interspacer layers between the lead lamella.

In this manner, a 2D anti-scatter grid is provided in a cost effective manner, that builds on existing 1D grid manufacture, but provides the secondary septa walls that provide the 2D structure in a completely new way, via appropriately locating columnar structures to form secondary septa walls.

In an example, the plurality of columnar structures extend in a direction substantially perpendicular to the plurality of primary septa walls.

It is to be noted that the secondary septa walls may only be perpendicular to the primary septa wall in the centre of a focused 2D grid (whereas, septa in unfocused 2D grids, are perpendicular everywhere). For a focused 2D grid, in going from the center to the corners of a large-area focused 2D grid, the primary and secondary walls become increasingly non-perpendicular. This is what is meant by "substantially perpendicular" and the skilled person would appreciate that this means with respect to both focused and unfocused 2D grids.

In an example, the plurality of secondary septa walls are comprised within a plurality of sheets. Between each adjacent pair of walls of the plurality of primary septa walls a sheet of the plurality of sheets is located.

In an example, the plurality of sheets are one of paper, carbon, polymer, insulator material, composite material, reinforced material, low-weight material, or aluminium or other low-weight metal.

In an example, the plurality of secondary septa walls are formed from a plurality of lines of the plurality of columnar structures.

In an example, the plurality of columnar structures are located in holes in the plurality of sheets.

In an example, two or more of the secondary septa walls in each sheet of the plurality of sheets are angled one to the other.

In an example, the two or more of the secondary septa walls in each sheet of the plurality of sheets are angled towards a common point or line in space.

In a second aspect, there is provided a method of manufacturing an X-ray anti-scatter grid, the X-ray anti-scatter grid comprising a plurality of primary septa walls, and a plurality of secondary septa walls, wherein the plurality of primary septa walls comprise an X-ray absorbing material. The method comprises arranging the plurality of primary septa walls substantially parallel to one another; and forming each secondary septa wall of the plurality of secondary septa walls from a plurality of columnar structures extending between the plurality of primary septa walls; and locating the plurality of secondary septa walls between adjacent pairs of walls of the plurality of primary septa walls such that each secondary septa wall is located between an adjacent pair of walls of the plurality of primary septa walls. The plurality of columnar structures comprise an X-ray absorbing material.

In an example, the method comprises forming the plurality of secondary septa walls within a plurality of sheets, and locating a sheet of the plurality of sheets between each adjacent pair of walls of the plurality of primary septa walls.

In an example, the method comprises forming the plurality of columnar structures in holes in the plurality of sheets.

In an example, the method comprises forming the plurality of columnar structures by printing into the plurality of holes.

In other words, secondary grid septa walls are introduced in the interspacer layers between the primary 1D septa walls of for example lead lamella, where the secondary septa walls are formed from columnar structures. This is done by controlled removal of material from the interspacer layer (e.g. by laser ablation), followed by accurate filling of the empty spaces with an X-ray absorbing material (e.g. by ink jetting/printing).

Thus, proven, well-established 1D grid manufacturing technology can be utilized to create a 1D ASG structure and laser drilling and printing technology used in a completely new way to generate an interspacer material for the 1D structure that turns that 1D structure into a 2D anti-scatter grid structure. Thus, a 2D ASG can be manufactured through the introduction of the minimal possible modifications to current 1D grid manufacturing processes, providing for a cost effective and flexible manner of fabricating 2D ASGs.

In an example, the method comprises machining back at least one surface of each sheet of the plurality of sheets.

In a third aspect, there is provided a method of manufacturing a plurality of secondary septa walls for an X-ray anti-scatter grid. The method comprising forming each secondary septa wall of the plurality of secondary septa walls from a plurality of columnar structures. The plurality of columnar structures comprise an X-ray absorbing material, and the plurality of columnar structures of each secondary septa wall are configured to extend between a pair of adjacent walls of a plurality of primary septa walls of the X-ray anti-scatter grid.

In an example, the method comprises forming the plurality of secondary septa walls in a sheet.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
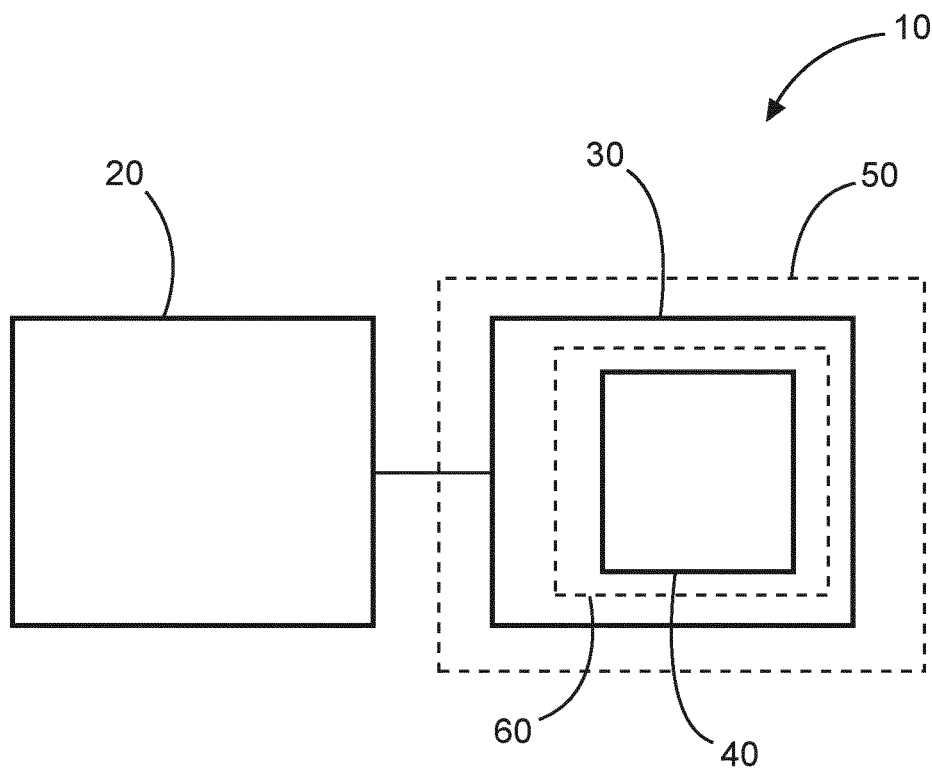
FIG. 1 shows a schematic set up of the composing features of an X-ray anti-scatter grid.
Figure 2:
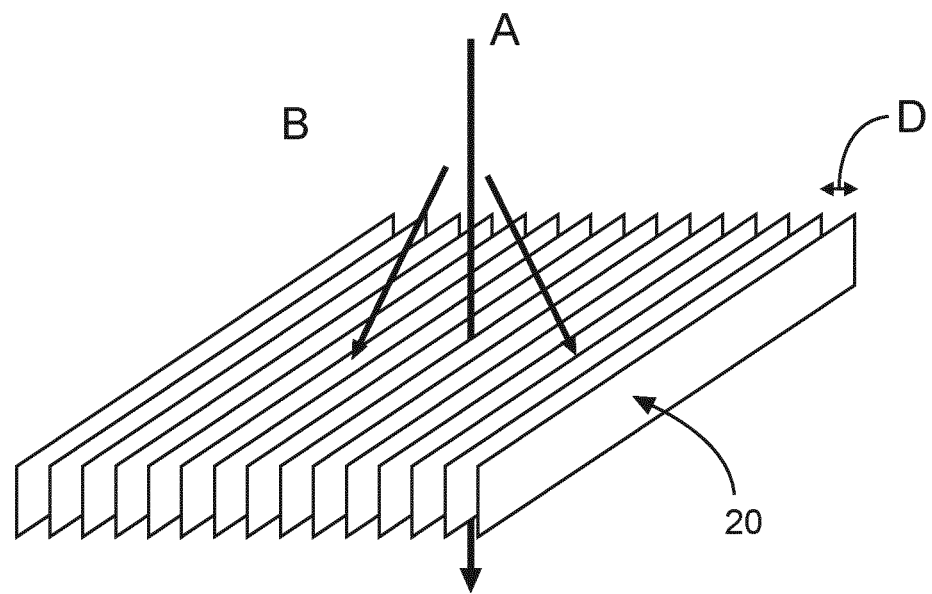
FIG. 2 shows an example of a 1D X-ray anti-scatter grid.
Figure 3:
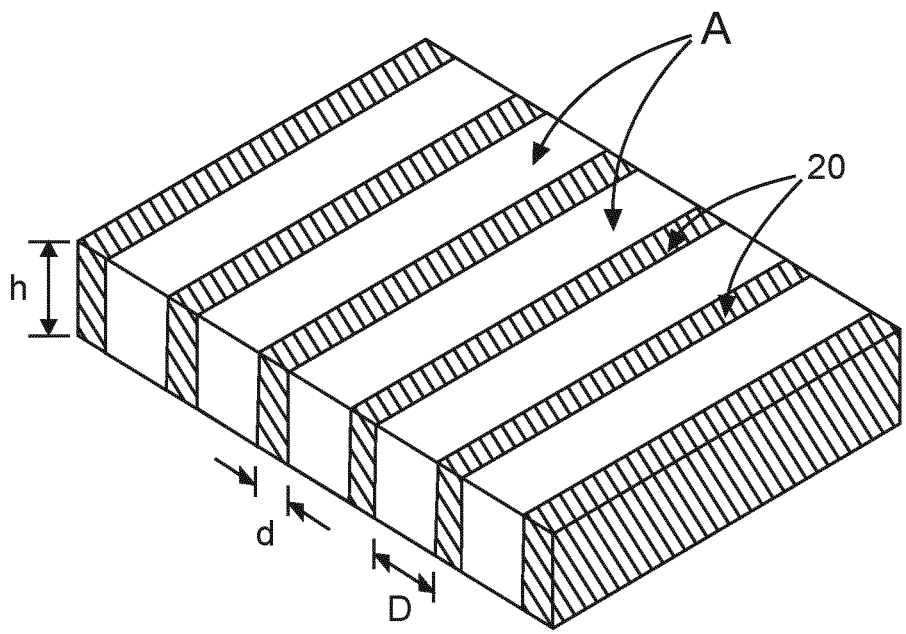
FIG. 3 shows an example of a 1D X-ray anti-scatter grid.
Figure 4A:
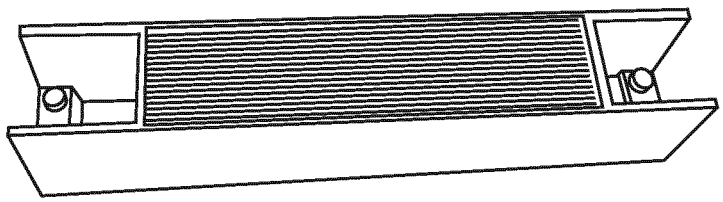
FIGS. 4A-D show examples of 1D X-ray and 2D anti-scatter grids.
Figure 4B:
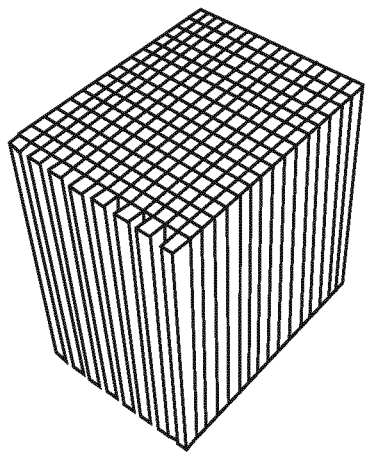
Figure 4C:
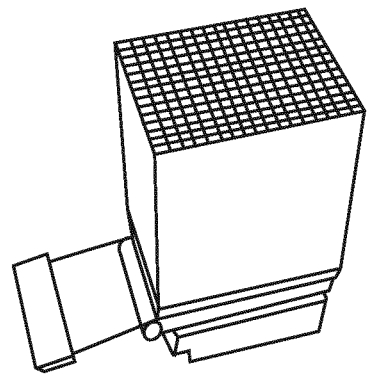
Figure 4D:
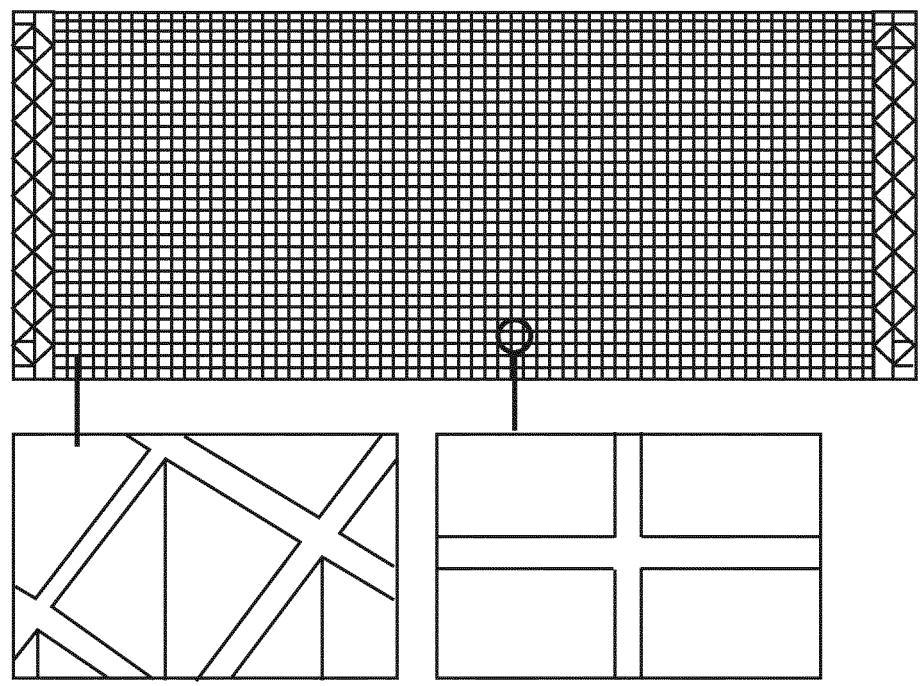

FIG. 1 shows an example of an X-ray anti-scatter grid 10, where essential features are shown in solid lines and optional features are shown in dashed lines. The X-ray anti-scatter grid is a 2D anti-scatter grid and comprises a plurality of primary septa walls 20, and a plurality of secondary septa walls 30. The plurality of primary septa walls comprise an X-ray absorbing material. The plurality of primary septa walls are substantially parallel to one another.

The plurality of secondary septa walls are located between adjacent pairs of walls of the plurality of primary septa walls such that each secondary septa wall is located between an adjacent pair of walls of the plurality of primary septa walls. Each secondary septa wall of the plurality of secondary septa walls is formed from a plurality of columnar structures 40 extending between the plurality of primary septa walls. The plurality of columnar structures comprise an X-ray absorbing material.

In an example, the primary septa walls are made of lead.

In an example, each columnar structure has a length substantially equal to a spacing between adjacent pairs of primary septa walls.

In an example, each columnar structure has a circular cross section.

In an example, each columnar structure has an oval cross-section.

In an example, each columnar structure has a constant cross-section.

In an example, each columnar structure has a varying cross section.

According to an example, the plurality of columnar structures extend in a direction substantially perpendicular to the plurality of primary septa walls.

According to an example, the plurality of secondary septa walls are comprised within a plurality of sheets 50. Between each adjacent pair of walls of the plurality of primary septa walls a sheet of the plurality of sheets is located.

According to an example, the plurality of sheets are one of paper, carbon, polymer, insulator material, composite material, reinforced material, low-weight material, or Aluminium or other low-weight metal.

According to an example, the plurality of secondary septa walls are formed from a plurality of lines of the plurality of columnar structures.

In an example, each secondary septa wall comprises a zig-zag line of columnar structures.

In an example, each secondary septawall comprises a plurality of lines of columnar structures.

According to an example, the plurality of columnar structures are located in holes 60 in the plurality of sheets.

In an example, the plurality of holes are formed by laser drilling/laser ablation.

In an example, the plurality of columnar structures are formed by printing into the plurality of holes.

In an example, the plurality of columnar structures are formed by ink jet printing into the plurality of holes.

In an example, the plurality of columnar structures are formed by screen printing into the plurality of holes.

According to an example, two or more of the secondary septa walls in each sheet of the plurality of sheets are angled one to the other.

According to an example, the two or more of the secondary septa walls in each sheet of the plurality of sheets are angled towards a common point or line in space.

A manufacturing method can be used to fabricate an X-ray anti-scatter grid. The X-ray anti-scatter grid once fabricated comprises a plurality of primary septa walls, and a plurality of secondary septa walls that comprise an X-ray absorbing material. The plurality of primary septa walls comprise an X-ray absorbing material. The method comprises arranging the plurality of primary septa walls substantially parallel to one another. The method then involves forming each secondary septa wall of the plurality of secondary septa walls from a plurality of columnar structures extending between the plurality of primary septa walls, and locating the plurality of secondary septa walls between adjacent pairs of walls of the plurality of primary septa walls such that each secondary septa wall is located between an adjacent pair of walls of the plurality of primary septa walls.

In an example the method comprises forming the plurality of columnar structures such that they extend in a direction substantially perpendicular to the plurality of primary septa walls According to an example, the method comprises forming the plurality of secondary septa walls within a plurality of sheets, and locating a sheet of the plurality of sheets between each adjacent pair of walls of the plurality of primary septa walls.

In an example, the plurality of sheets are one of paper, carbon, polymer, insulator material, composite material, reinforced material, low-weight material, or Aluminium or other low-weight metal In an example, the plurality of secondary septa walls are formed from a plurality of lines of the plurality of columnar structures.

According to an example, the method comprises forming the plurality of columnar structures in holes in the plurality of sheets.

In an example, the method comprises laser drilling the plurality of holes in the plurality of sheets.

According to an example, the method comprises forming the plurality of columnar structures by printing into the plurality of holes.

In an example, the ink or paste used for printing is loaded with tungsten and/or bismuth containing particles.

According to an example, the method comprises machining back at least one surface of each sheet of the plurality of sheets.

In an example, two or more of the secondary septa walls in each sheet of the plurality of sheets are angled one to the other.

In an example, the two or more of the secondary septa walls in each sheet of the plurality of sheets are angled towards a common point or line in space.

It will be appreciated that the columnar structures that will be used to make the secondary septa walls can be fabricated separately to the anti-scatter grid. Therefore, a method of manufacturing a plurality of secondary septa walls for an X-ray anti-scatter grid comprises forming each secondary septa wall of the plurality of secondary septa walls from a plurality of columnar structures. The plurality of columnar structures comprise an X-ray absorbing material, and the plurality of columnar structures of each secondary septa wall are configured to extend between a pair of adjacent walls of a plurality of primary septa walls of the X-ray anti-scatter grid.

In an example the method comprises forming the plurality of columnar structures is a direction such that they will extend in a direction perpendicular to the plurality of primary septa walls According to an example, the method comprises forming the plurality of secondary septa walls in a sheet.

In an example, the sheet is configured to be located between adjacent primary septa walls of a 1D anti-scatter grid to form a 2D anti-scatter grid structure.

In an example, the sheet is one of paper, carbon, polymer, insulator material, composite material, reinforced material, low-weight material, or Aluminium or other low-weight metal.

In an example, the plurality of secondary septa walls are formed from a plurality of lines of the plurality of columnar structures.

In an example, the method comprises forming the plurality of columnar structures in holes in the sheet.

In an example, the method comprises laser drilling the plurality of holes in the sheet.

In an example, the method comprises forming the plurality of columnar structures by printing into the plurality of holes.

In an example, the method comprises machining back at least one surface of the sheet.

In an example, the method comprises forming at least two or more of the secondary septa walls in the sheet at an angled one to the other.

In an example, the method comprises forming the two or more of the secondary septa walls in the sheet at an angle towards a common point or line in space.

The X-ray anti-scatter grid, the method of manufacturing an X-ray anti-scatter grid, and the method of manufacturing a plurality of secondary septa walls for an X-ray anti-scatter grid will now be described in specific detail, where reference is made to FIGS. 5-9, involving the creation of secondary septa walls of an X-ray 2D anti-scatter grid in the interspacer sheet.

Figure 5:
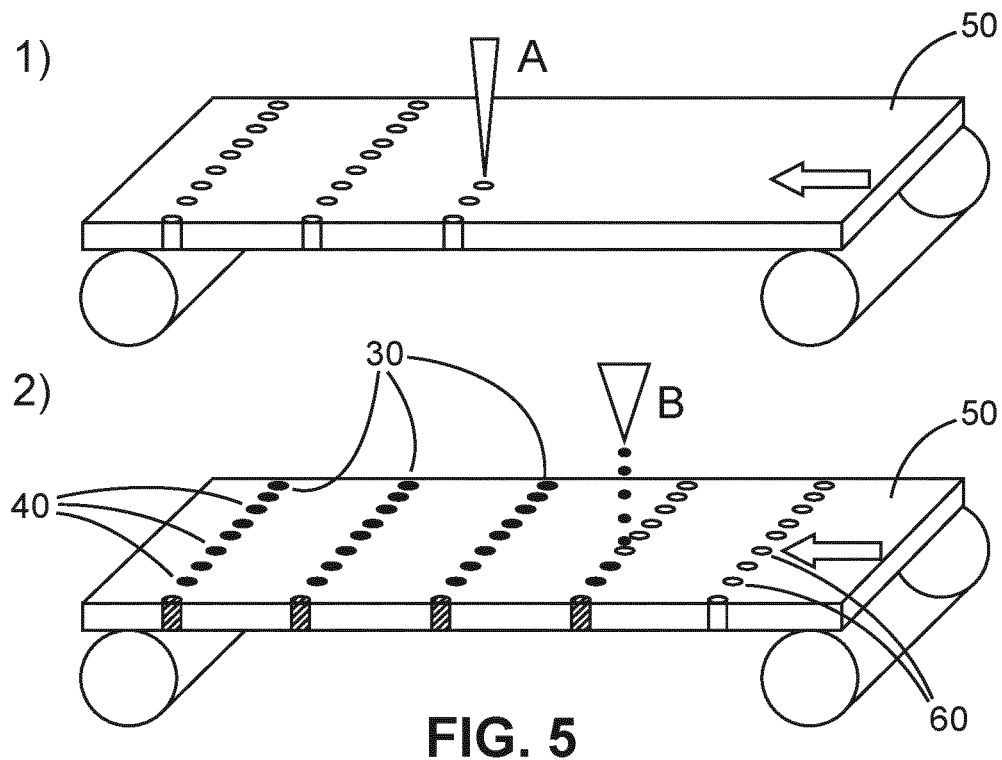
FIG. 5 shows schematic representations of processing of a sheet of fiber interspace material to provide a plurality of columnar structures to form secondary septa walls of an X-ray 2D anti-scatter grid.

FIG. 5 shows an example of processing of a sheet of fibre interspacer material to provide a plurality of columnar structures to form secondary septa walls of an X-ray 2D anti-scatter grid. Thus, in effect an additional two-step roll-to-roll (R2R) process can be inserted into the current 1D ant-scatter grid production line. The process involves the following steps shown diagrammatically in the top and bottom parts of FIG. 5:

Laser perforation (ablation) with a laser beam "A" of cylindrical through-holes 60 in interspacer/fiber layer 50 (preferably before paper (or other sheet material) planing), followed by:

Filling the holes by inkjet or screen printing with an inkjet head "B" of a high-Z material into the created holes to form secondary septa walls 30 made from columnar structures. The ink or paste used is loaded with tungsten and/or bismuth (or other X-ray ray absorbing material) particles, this can if necessary be followed by:

Curing and drying.

Figure 6:
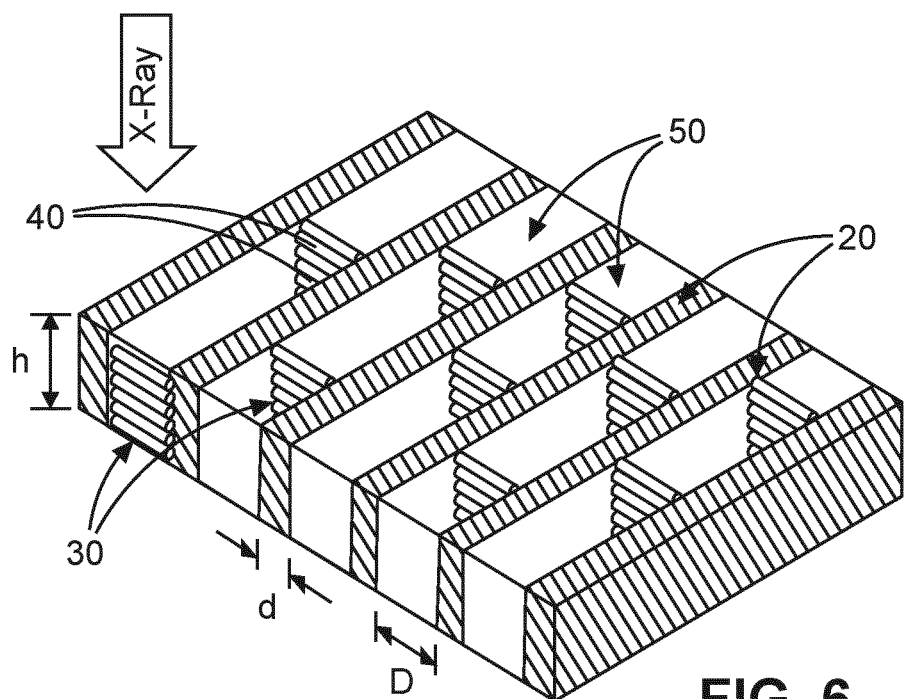
FIG. 6 shows an example of an X-ray 2D anti-scatter grid.
Figure 7:
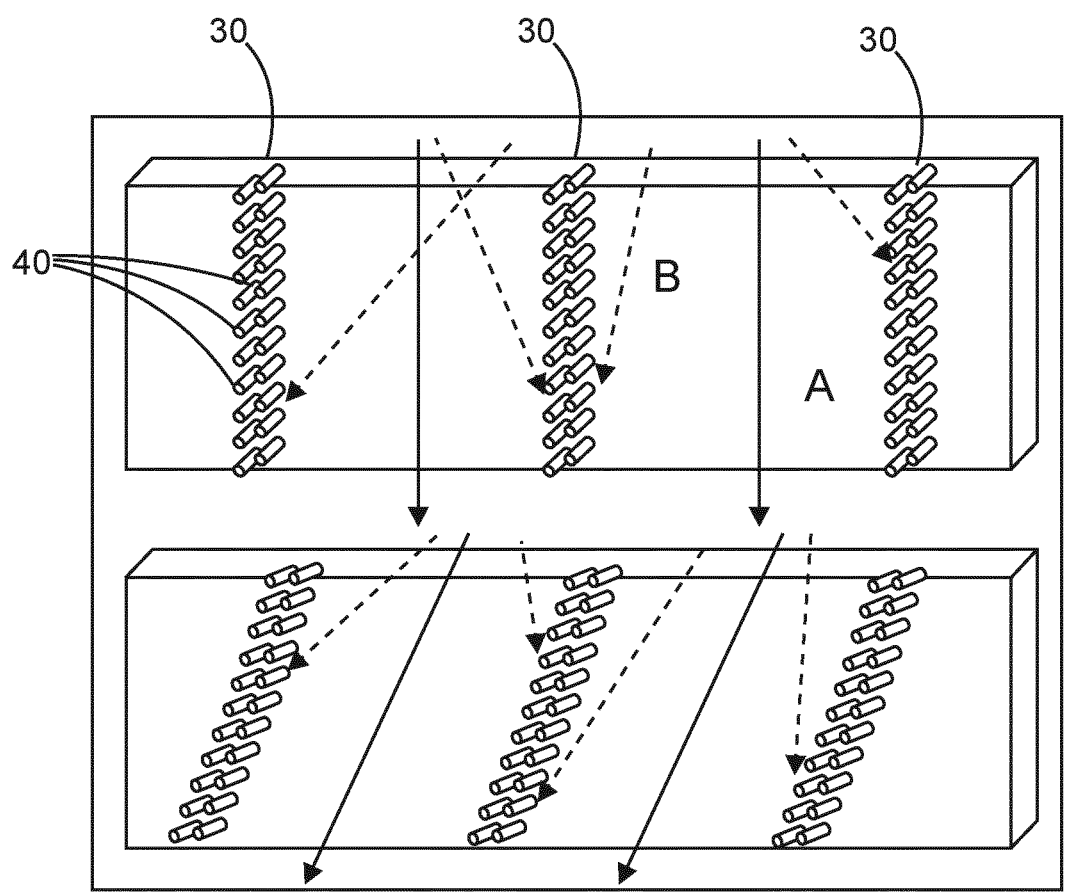
FIG. 7 shows examples of an interspacer sheet with a plurality of columnar structures forming secondary septa walls of an X-ray 2D anti-scatter grid.
Figure 8:
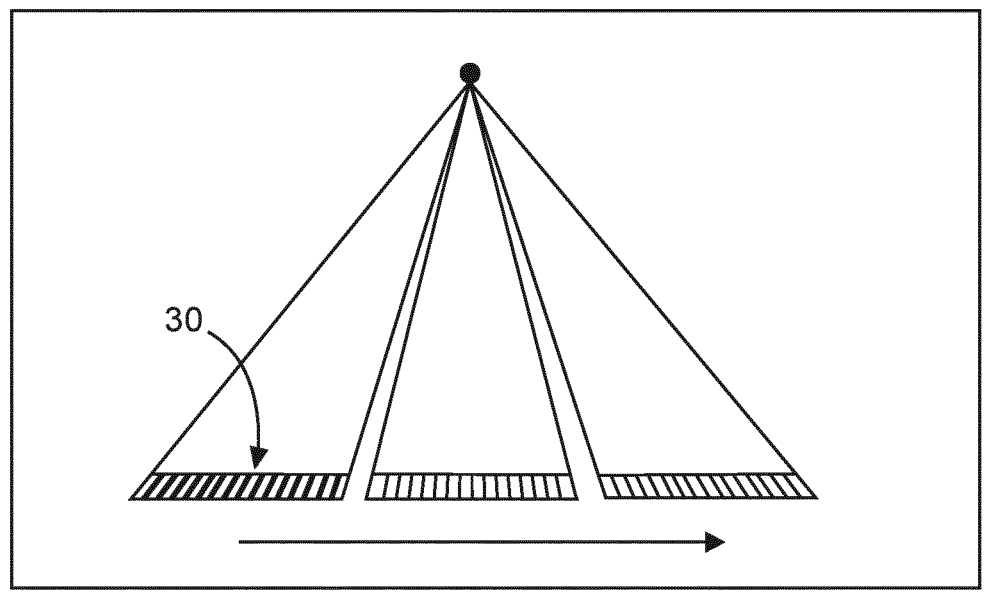
FIG. 8 shows angled secondary septa walls in an interspacer sheet of an X-ray 2D anti-scatter grid.

FIG. 6 illustrates schematically how a standard 1D grid composed of lead lamella 20 can be transformed to a 2D grid. Secondary septa walls 30 are introduced into the interspacer layer (for example a sheet of paper or Aluminium) 50 by creation of vertical lines of perforated (cylindrical) holes in the interspacer material, followed by filling them with X-ray absorbing (high-Z) material to form columnar structures 40. These secondary septa walls 30 are oriented perpendicular to the primary septa walls 20, consisting of lead lamella, and thereby generate the second dimension in the 1D grid structure. The secondary septa walls 30 formed by the columnar structures 40 are shown schematically, highlighting the cylindrical nature of their structure in this example and can be oriented vertically as shown in the lamella at the front left wall. However, the columnar structures can be angled, as shown in FIG. 7, and the other secondary septa shown in FIG. 6 are only shown in a representative manner, with their circular ends visible, but this is not actually the case as these ends are actually behind the lead lamella 20.

The design and distribution of holes across the interspacer layer can be varied to optimized ASG performance for a specific imaging application. For example, FIG. 7 shows two examples of secondary septa walls 30 (top: unfocused grid, bottom: focused grid) made from columnar structures 40, where primary X-rays are shown at "A" and scattered X-rays shown at "B". FIG. 7 illustrates that primary X-ray transmission of the ASG can be increased by adapting orientation of hole lines ('focus") parallel to the incident primary X-ray beam across the entire length of the interspacer (from one side of the ASG to the other). This is shown in further detail in FIG. 8, where the secondary septa walls can point towards the X-ray source to maximize throughput. It is to be noted that the secondary septa walls in each interspacer do not need to be perfectly aligned between interspacer layers, for example as shown in FIG. 6.

Figure 9:
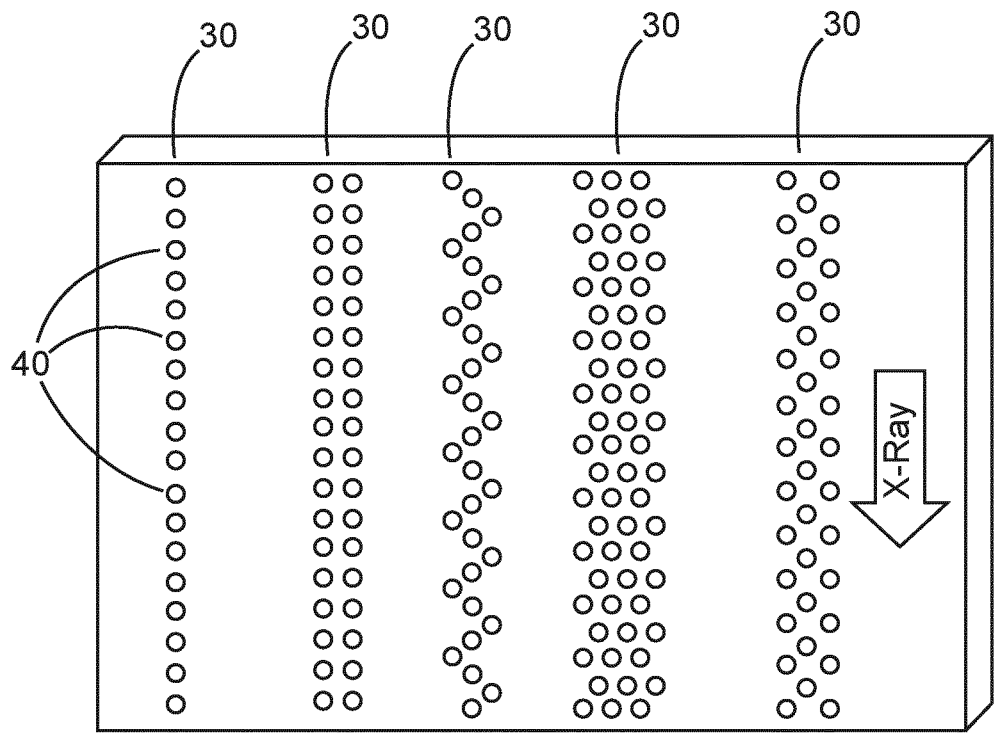
FIG. 9 shows an example of an interspacer sheet with a plurality of columnar structures forming secondary septa walls of an X-ray 2D anti-scatter grid.

FIG. 9 illustrates various examples of hole line patterns from top to bottom of the interspacer layer. Each through-hole will form a cylinder with diameter between 10 and 50 μm (say 25 μm) and height between 50 and 500 μm (say 200 μm), which equals the interspacer layer thickness. It is to be understood that as the cylinders may not have a constant cross section and could be wider at the front surface than the rear, and indeed an oval shaped laser beam can be used to make oval shaped holes and thus oval shaped columnar structures can be fabricated to form secondary septa walls. A line of filled holes forms the secondary septa walls, which can be designed in such a way to maximize absorption of scattered X-rays in the plane of the interspacer (parallel to the lead lamella), while still maintaining a large transmission of primary X-rays. The introduction of secondary septa walls in a 1D grid may also enable to reduce thickness of the primary septa walls (lead lamella), while ASG performance of the 2D grid is higher compared to the 1D grid.

It is to be noted that other embodiments are possible:

In addition to paper, other ASG interspacer materials are possible, such as polymers (e.g. polyetherimides, polyimides, and polycarbonate) or Aluminum, which may have even better dimensional stability than paper.

In addition to the hole lines, other designs of the secondary septa walls in the interspacer layer are possible, such as dotted, dashed, zigzag and/or straight trenches. Also, depth of holes or trenches may be smaller than the interspacer thickness. For example, it is possible to laser ablate blind trenches from both sides of the interspacer paper, instead of laser ablating lines of through-holes from a single side of the interspacer paper, in order to make the secondary septa walls. Thus, a line of blind holes can be drilled from one side of the interspacer paper and a line of blind holes can be drilled from the other side, and these can for example be staggered down the interspacer paper. In R2R processing even continuous through-trenches across the complete width of the interspacer roll are possible when the interspacer is supported by a solid carrier foil. Specific secondary septa wall designs may be more easily manufactured in sheet-to-sheet (S2S) or piece-to-piece (P2P) processing of interspacer material, as compared to R2R processing.

Regarding the fabrication technique, this builds on the large industrial equipment base that is used for (1) laser perforation of paper (or plastics) in the packaging industry for example used for cigarette fabrication (or fruit packing) and (2) ink jet printing as used in flexible printed electronics. These two processes can be integrated to facilitate manufacturing, in particular to achieve high alignment accuracy of hole ablation and hole filling. For example, the required basic components (laser beam, optical components, inkjet head and ink supply) can be assembled into a single process head, which only needs small sideway movements when combined with controlled step-and-shoot movement of the interspacer.

It can be beneficial to execute the R2R process before interspacer planing (here planning refers to accurate thinning of the incoming paper (or other sheet material) to the required thickness), as this can have a low impact on the current 1D grid production process. Furthermore, subsequent planing can remove undesired laser debris and superfluous printing material from the surface of the interspacer material. Thus, the holes need not be laser drilled or ablated all the way through the layer or interspace material before filling of the high-Z ink, because the back surface can be planed back to reveal the columnar structure prior to the insertion of the layer between the 1D primary septa walls.

Thus in summary, the following features/advantages of the 2D XL anti-scatter grid and its method of manufacture includes:

Fabrication is compatible with 1D grid manufacturing process

High anti-scatter performance (low SPR, high CNR)

Enables realisation of high-resolution CT detector (pixel pitch<<1 mm) due to thin grid septa walls. This will be hard to achieve using 2D DMLS grid because of its thick (≈100 μm) septa walls.

Capability to cover large-area X-ray and (value) CT detector, no grid tiling is needed Low-cost alternative to expensive 2D tungsten DMLS grid Lower weight than heavy 2D tungsten DMLS grid No grid line artifacts in X-ray image due to thin grid septa walls in both directions (parallel and perpendicular to lead lamella) and absence of grid tiling.

No loss of clinically relevant details in x-ray image due to thin grid septa walls Enables grid bending (perpendicular to lead lamella) for curved detectors It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray anti-scatter grid, comprising:
a plurality of primary septa walls; and
a plurality of secondary septa walls;
wherein the plurality of primary septa walls comprise an X-ray absorbing material;
wherein the plurality of primary septa walls are substantially parallel to one another;
wherein the plurality of secondary septa walls are located between adjacent pairs of walls of the plurality of primary septa walls such that each secondary septa wall is located between an adjacent pair of walls of the plurality of primary septa walls,
wherein each secondary septa wall of the plurality of secondary septa walls is formed from a plurality of columnar structures extending between the plurality of primary septa walls, wherein the plurality of columnar structures comprise an X-ray absorbing material, and
wherein the plurality of secondary septa walls are arranged within a plurality of sheets, wherein a sheet of the plurality of sheets is located between each adjacent pair of walls of the plurality of primary septa walls.

2. The anti-scatter grid according to claim 1, wherein the plurality of columnar structures extend in a direction substantially perpendicular to the plurality of primary septa walls.

3. The anti-scatter grid according to claim 1, wherein the plurality of sheets are one of paper, carbon, polymer, insulator material, composite material, reinforced material, low-weight material, aluminum, or other low-weight metal.

4. The anti-scatter grid according to claim 1, wherein the plurality of secondary septa walls are formed from a plurality of lines of the plurality of columnar structures.

5. The anti-scatter grid according to claim 1, wherein the plurality of columnar structures are located in holes in the plurality of sheets.

6. The anti-scatter grid according to claim 1, wherein two or more of the secondary septa walls in each sheet of the plurality of sheets are angled one to the other.

7. The anti-scatter grid according to claim 6, wherein the two or more of the secondary septa walls in each sheet of the plurality of sheets are angled towards a common point or line in space.

8. A method of manufacturing an X-ray anti-scatter grid, comprising:
providing a plurality of primary septa walls and a plurality of secondary septa walls, wherein the plurality of primary septa walls comprise an X-ray absorbing material;
arranging the plurality of primary septa walls substantially parallel to one another;
forming the plurality of secondary septa walls within a plurality of sheets;
locating a sheet of the plurality of sheets between each adjacent pair of walls of the plurality of primary septa walls;
forming each secondary septa wall of the plurality of secondary septa walls from a plurality of columnar structures extending between the plurality of primary septa walls; and
locating the plurality of secondary septa walls between adjacent pairs of walls of the plurality of primary septa walls such that each secondary septa wall is located between an adjacent pair of walls of the plurality of primary septa walls, wherein the plurality of columnar structures comprise an X-ray absorbing material.

9. The method according to claim 8, further comprising forming the plurality of columnar structures in holes in the plurality of sheets.

10. The method according to claim 9, further comprising forming the plurality of columnar structures by printing into the plurality of holes.

11. The method according to claim 9, further comprising machining back at least one surface of each sheet of the plurality of sheets.

* * * * *